United States Patent
Agee et al.

(10) Patent No.: US 9,062,257 B1
(45) Date of Patent: Jun. 23, 2015

(54) ENHANCED GTL PROCESS

(71) Applicant: Emerging Fuels Technology, Inc., Tulsa, OK (US)

(72) Inventors: Kenneth L. Agee, Tulsa, OK (US); Kym B. Arcuri, Tulsa, OK (US); Rafael L. Espinoza, Tulsa, OK (US)

(73) Assignee: EMERGING FUELS TECHNOLOGY, INC., Tulsa, OK (US)

( * ) Notice: Subject to any disclaimer, the term of this patent is extended or adjusted under 35 U.S.C. 154(b) by 0 days.

(21) Appl. No.: 14/546,109

(22) Filed: Nov. 18, 2014

Related U.S. Application Data

(60) Provisional application No. 61/906,102, filed on Nov. 19, 2013.

(51) Int. Cl.
*C10G 2/00* (2006.01)
*C07C 1/04* (2006.01)

(52) U.S. Cl.
CPC .......... *C10G 2/32* (2013.01); *C10G 2/341* (2013.01); *C07C 1/04* (2013.01)

(58) Field of Classification Search
CPC .................................. C10G 2/32; C10G 2/341
USPC ........................................................ 518/700
See application file for complete search history.

(56) References Cited

U.S. PATENT DOCUMENTS

| | | | |
|---|---|---|---|
| 4,579,985 A | 4/1986 | Minderhoud | |
| 4,587,008 A | 5/1986 | Minderhoud | |
| 4,628,133 A | 12/1986 | Minderhoud | |
| 6,043,288 A | 3/2000 | DeGeorge | |
| 6,147,126 A | 11/2000 | DeGeorge | |
| 6,512,018 B2 | 1/2003 | Kennedy | |
| 6,696,501 B2 | 2/2004 | Schanke | |
| 6,784,212 B2 | 8/2004 | Steynberg | |
| 6,958,363 B2 | 10/2005 | Espinoza | |
| 7,004,985 B2 * | 2/2006 | Wallace et al. | 48/198.3 |
| 7,250,450 B2 | 7/2007 | Fenouil | |
| 7,717,971 B2 | 5/2010 | Aasberg-Petersen | |
| 7,879,919 B2 | 2/2011 | Ernst | |
| 7,910,629 B2 | 3/2011 | Minta | |
| 8,106,102 B2 | 1/2012 | Steynberg | |

FOREIGN PATENT DOCUMENTS

WO    WO 2011141635 A1 * 11/2011

* cited by examiner

*Primary Examiner* — Sudhakar Katakam
(74) *Attorney, Agent, or Firm* — Head, Johnson & Kachigian, P.C.

(57) ABSTRACT

A process for converting carbonaceous materials or light hydrocarbon gases into products comprising predominately C5+ hydrocarbons. The process converts the feedstock into synthesis gas comprising hydrogen and carbon monoxide and then uses the Fischer-Tropsch reaction to produce heavy hydrocarbons. A small excess of hydrogen is produced in the syngas generator or by water gas shift for use in product upgrading and for blending with Fischer-Tropsch tail gas for recycle back to syngas generation. A portion of the Fischer-Tropsch tail gas is used as fuel, thus purging combustible light gases and $CO_2$ from the tail gas. Hydrogen rich purge gas is blended into the remaining tail gas resulting in a recycle stream that is returned to the syngas generator. The tail gas components are therefore efficiently used to produce more products.

16 Claims, 2 Drawing Sheets

ENHANCED GTL PROCESS

CROSS REFERENCE TO RELATED APPLICATIONS

This application claims priority to U.S. Provisional Application Ser. No. 61/906,102, filed Nov. 19, 2013, which is incorporated herein by reference.

BACKGROUND OF THE INVENTION

1. Field of Invention

The present invention relates to an enhanced gas to liquids process for the production of heavy hydrocarbon products from carbonaceous feeds such as coal, biomass, municipal waste and/or light gaseous hydrocarbons such as natural gas, associated gas, coal seam gas, landfill gas, or biogas.

2. Related Art

Various processes are known for the conversion of carbonaceous feeds and/or light hydrocarbon containing gases into normally liquid products such as methanol, higher alcohols and hydrocarbon fuels and chemicals, particularly paraffinic hydrocarbons. Such processes are directed at the objective of adding value to the feedstock by making a transportable, more valuable product such as diesel fuel, jet fuel, or chemicals such as base oils, solvents, or drilling fluids.

The Fischer-Tropsch process can be used to convert such carbonaceous feeds and/or gaseous light hydrocarbon products into more valuable, easily transportable liquid hydrocarbon products and chemicals. The feedstock is first converted to synthesis gas comprising carbon monoxide and hydrogen. The synthesis gas is then converted to heavy hydrocarbon products over a Fischer-Tropsch catalyst. The heavy hydrocarbon products can be subjected to further workup or processing by hydroprocessing such as hydrocracking and/or hydroisomerization and distillation resulting in, for example, a high yield of high quality middle distillate products such as jet fuel or diesel fuel. The heavy hydrocarbon products can thereafter also be upgraded to specialty products such as solvents, drilling fluids, waxes or lube base oils due to the high purity of the Fischer-Tropsch products.

Processes that convert carbonaceous feeds and/or light hydrocarbons to heavier hydrocarbon products generally have at least three steps: 1) conversion of the feedstock to synthesis gas comprising carbon monoxide and hydrogen; 2) conversion of the synthesis gas to heavy hydrocarbons via a Fischer-Tropsch reaction; and 3) hydroprocessing the heavy hydrocarbon product to one or more finished hydrocarbon products.

The efficiency and effectiveness of the subject process depends not only on the effectiveness of the three steps, but also on how the steps are integrated. Efficient utilization of tail gas generated during the Fischer-Tropsch reaction reduces the amount of natural gas feed required. The present invention is directed to operate the Fischer-Tropsch reactors below the stoichiometric $H_2$:CO ratio, resulting in a carbon rich tail gas which is partially purged as fuel gas. A hydrogen rich purge stream from hydroprocessing is added to the remaining tail gas so that the recycle stream is relatively high in hydrogen which results in improved operation of the syngas generator.

The present invention is directed to an efficient method of integration of the process steps comprising:

a process to convert carbonaceous feeds and/or light hydrocarbon gases into heavy hydrocarbon products which process comprises:

a) converting a feedstock of carbonaceous materials and/or light hydrocarbon gases into synthesis gas comprising hydrogen ($H_2$) and carbon monoxide (CO);

b) separating a part of the hydrogen from the synthesis gas of step (a);

c) passing all or a portion of the synthesis gas after hydrogen separation over a cobalt based Fischer-Tropsch catalyst in a Fischer-Tropsch reactor resulting in production of heavy hydrocarbon products, water and a tail gas comprising mainly CO, $CO_2$, $H_2$, and C4– hydrocarbons and inert gases if present in the syngas feed;

d) using a portion of the $H_2$ of step (b) for hydroprocessing the Fischer-Tropsch hydrocarbon products;

e) using a portion of the Fischer-Tropsch tail gas as fuel; and f) mixing all or a part of the any remaining $H_2$ rich stream from step (b) not used for hydroprocessing with all or a part of any remaining Fischer-Tropsch tail gas not used as fuel and recycling this mixed gas stream to step (a).

U.S. Pat. Nos. 4,579,985, 4,587,008, and 4,628,133 each describe a process for the preparation of hydrocarbons wherein a light hydrocarbon stream and a recycle stream are reacted with steam in a steam methane reformer ("SMR") to produce synthesis gas. The synthesis gas is reacted in a Fischer-Tropsch reaction to produce a mixed hydrocarbon stream including unreacted synthesis gas and light hydrocarbons. A portion of the hydrogen is removed from the tail gas and all or a portion of the gaseous stream of light hydrocarbons and unreacted synthesis gas after hydrogen separation is recycled to combine with the feed gas for feed to the SMR.

In the present invention, step b refers to the removal of hydrogen from the syngas generation in step a. It is advantageous to remove hydrogen immediately after syngas generation since this stream typically contains the highest partial pressure (concentration) and hence involves the lowest capital and energy cost for removal. The preferred amount of hydrogen to remove depends upon achieving the desired H2/CO ratio for the FT synthesis (step c) and to provide sufficient hydrogen for subsequent hydroprocessing of the FT liquids into final products (fuels, solvents, base oils, etc.). The appropriate amount of H2 for the syngas ratio adjustment depends on the configuration of the FT reactor system. Preferably, the net amount of hydrogen in the Fischer-Tropsch system, including any hydrogen added back, is enough to assure that the $H_2$:CO ratio in the Fischer-Tropsch tail gas will not drop below 0.5:1. A ratio below 0.5:1 may result in carbon build up on the catalyst and resulting loss of catalyst activity.

A portion of this hydrogen lean Fischer-Tropsch reactor tail gas is used as fuel gas. This tail gas stream contains $CO_2$ and serves to purge $CO_2$ from the system. Preferably, the excess hydrogen purged from the hydroprocessing step is not used as fuel so that a mixture of the remaining hydrogen and tail gas is recycled back to the syngas generation step. In a preferred embodiment, it is not necessary to remove $CO_2$ from the recycle loop. Such $CO_2$ removal adds capital and operating expense and is therefore undesirable.

U.S. Pat. No. 6,696,501 describes a method for conversion of natural gas to higher hydrocarbons comprising:

a) reacting natural gas with steam and oxygen in an ATR to produce synthesis gas;

b) passing the synthesis gas to a Fischer-Tropsch reactor where heavy hydrocarbon product, water and tail gas are produced;

c) separating the hydrocarbon product, water and tail gas;

d) reacting at least part of the tail gas stream with steam in a steam methane reformer ("SMR"); and e) adding the reformed tail gas to the syngas stream before the Fischer-Tropsch reactor.

The present invention does not require a separate reformer to efficiently recycle the tail gas.

U.S. Pat. No. 6,784,212 describes a process wherein synthesis product gases are separated in several steps and light gases are separated by pressure swing adsorption or are cryogenically separated such that CO and $H_2$ are concentrated and recycled to the Fischer-Tropsch reactor, a portion of which may be concentrated in purified hydrogen. Optionally, the light gases are all recycled to the syngas production unit with no hydrogen separation. In the cryogenic separation option, $CO_2$ is removed and vented.

The present invention does not use cryogenic or pressure swing adsorption technologies to separate tail gas components.

U.S. Pat. No. 7,250,450 describes a process wherein gaseous hydrocarbon feed is reacted with oxygen in a partial oxidation reactor and converted to synthesis gas. The synthesis gas is converted to hydrocarbon products in a Fischer-Tropsch reactor with a cobalt based catalyst. The hydrocarbon products are separated from the light components which are called a recycle stream, and $CO_2$ is removed from the recycle stream before it is sent back to the partial oxidation unit.

The present invention does not use $CO_2$ removal. It is an objective of the present invention to avoid $CO_2$ removal as it is costly.

Accordingly, the present invention is directed to an enhanced process for the production of heavy hydrocarbon products from carbonaceous materials and/or a light hydrocarbon gas wherein a hydrogen depleted Fischer-Tropsch tail gas is partially consumed as fuel, therefore, purging $CO_2$ from the system. The remaining tail gas is blended with a hydrogen purge stream and recycled back to syngas generation resulting in an enhanced process.

The present invention is also directed to an enhanced process resulting in increased production of heavy hydrocarbon products versus light hydrocarbon products.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for the purposes of exemplification.

Figure 1:
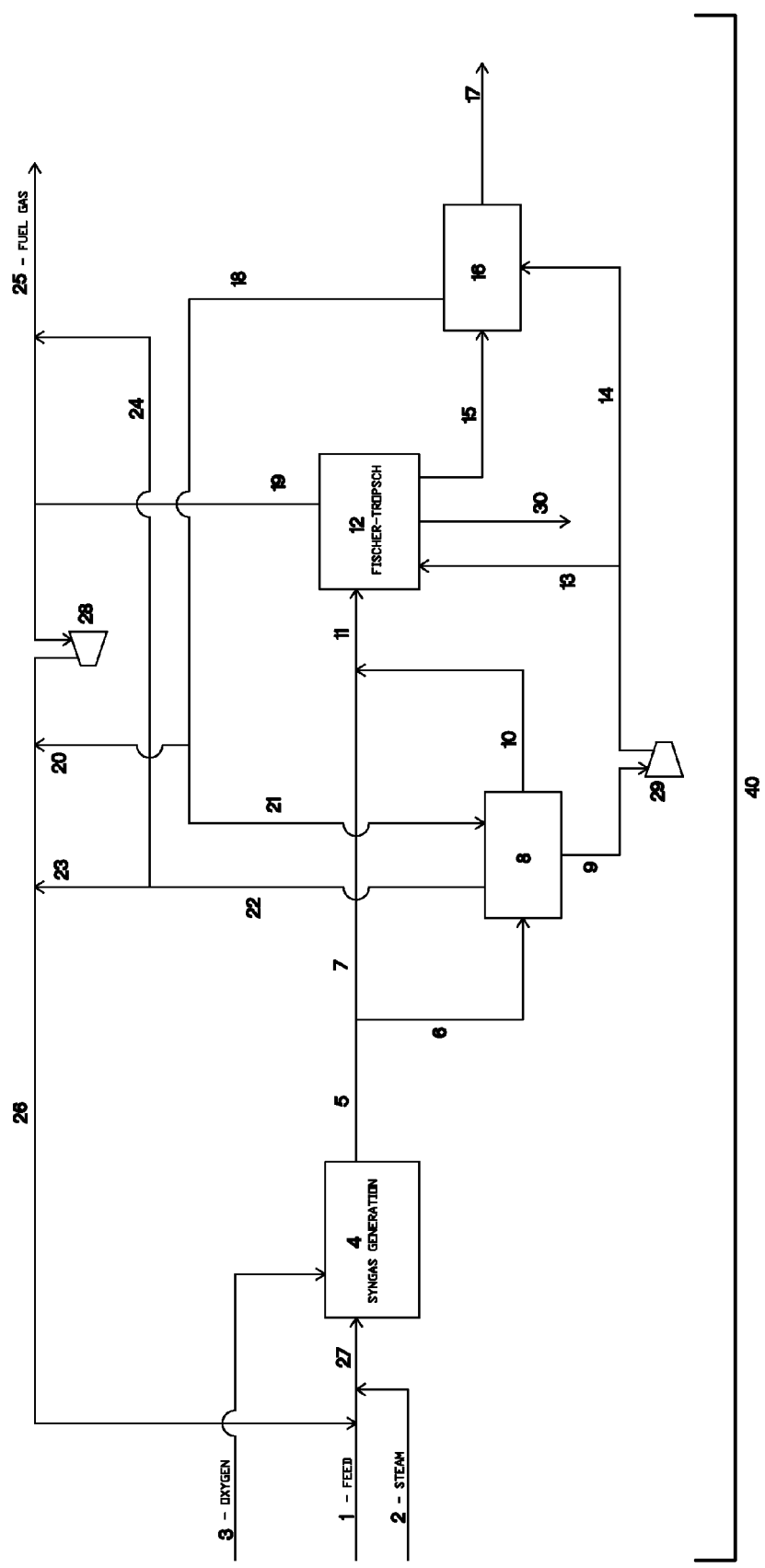
FIG. 1 illustrates a simple process diagram according to the present invention.

Referring to FIG. 1, process configuration 40 describes a preferred embodiment of the present invention, utilizing a carbonaceous feedstock such as coal. Biomass or municipal solid waste ("MSW") and/or a light gaseous feed such as natural gas, light hydrocarbon gases, associated gas, coal seam gas, landfill gas or biogas 1 are combined with a recycle stream 26, to be described in detail. Ethane and heavier components in the feed gas and/or recycle gas may be removed and/or there may be a pre-reformer before a syngas generator 4.

Steam 2 is optionally added to the feed stream 1 which is preheated before feeding to the syngas generator 4. In addition, an oxygen containing gas (3), preferably relatively pure oxygen, may be preheated before being fed to the syngas generator 4. The combined feed 1, recycle stream 26 and steam 2 is then fed to the syngas generator 4 which converts carbonaceous material to synthesis gas. The syngas generator may be any type of reformer or gasifier such as an autothermal reformer or a combination of partial oxidation and steam methane reforming. When the feedstock is a gaseous material only, the syngas generator is preferably an autothermal reformer.

Synthesis gas 5 is generated in the syngas generator 4. The syngas generator exit gas 5 is cooled and separated so that a portion of the syngas 6 is modified to adjust the $H_2$:CO ratio, if needed, and to purify hydrogen 9, for hydroprocessing unit 16. A hydrogen separation/purification unit 8 may comprise one or more stages of membrane separation, pressure swing adsorption ("PSA") or combinations thereof or any separation technology known to one skilled in the art. In this embodiment, a two stage hydrogen membrane followed by PSA is used in unit 8 and a hydrogen depleted retentate stream 10 is blended with syngas stream 7. The resulting stream 11 having a lower $H_2$:CO ratio than stream 7 is fed to a Fischer-Tropsch (FT) reactor 12. The Fischer-Tropsch reactor produces heavy hydrocarbon products, water and tail gas which are directed via line 15 to a hydroprocessing unit 16.

A relatively pure hydrogen stream 18 exits the hydroprocessing unit 16. A portion of hydrogen as shown in line 20 is separated from hydrogen stream 18. Hydrogen stream 20 is purged from the hydrogen stream 18. The resulting stream 21 is recycled to the hydrogen separation/purification unit 8. This high purity stream makes it easier to provide high purity hydrogen 9 to the hydroprocessing unit 16. The PSA purification system in unit 8 removes light hydrocarbon gases and $CO_2$ as shown at line 22 from the hydrogen stream. This stream can either be added to the tail gas recycle stream via line 23 or added to fuel gas 25 via line 24. The purge hydrogen stream 20 is thereafter recycled back as feed to the syngas generation unit 4.

The hydrogen stream 9 is compressed 29 and a portion 13 may be used to adjust the $H_2$:CO ratio between stages or within a Fischer-Tropsch recycle stream in the Fischer-Tropsch unit 12. The balance is sent to the hydroprocessing unit 16 via line 14.

Fischer-Tropsch unit 12 produces water 30, hydrocarbon products 15 and tail gas 19. The hydrocarbon products 15 is hydroprocessed and, optionally, distilled in hydroprocessing unit 16 to produce one or more finished products 17.

The Fischer-Tropsch tail gas 19 comprises light hydrocarbon gases, unreacted syngas and $CO_2$. A portion of this stream 25 is used as fuel gas thereby purging $CO_2$ from the system. The remaining tail gas is compressed 28 and blended with purge hydrogen stream 20 and optionally PSA discharge stream 23. This blended stream enriched in hydrogen relative to Fischer-Tropsch tail gas 19 and partially depleted of $CO_2$ is recycled via line 26 to produce more syngas in unit 4.

The products produced in the Fischer-Tropsch reactor are condensable hydrocarbon products, water, and tail gas comprising unreacted syngas, light hydrocarbons and $CO_2$. The desirable $H_2$:CO ratio of synthesis gas stream 11 may be set and controlled so that the $H_2$:CO ratio of tail gas stream 19 exiting the Fischer-Tropsch section is at least 0.5:1.

The Fischer-Tropsch unit 12 may be a single stage reactor with recycle or it may be two reactors in series with a recycle stream around one or both reactors, or it may be three reactors in series with recycle around all or some of the reactors. Any reactor type or configuration known to one skilled in the art may be used.

Optional hydrogen stream 13 may be used to adjust the inter stage $H_2$:CO ratio if multistage operation is employed in the Fischer-Tropsch section or to adjust a recycle stream around one or more reactors. Operating the Fischer-Tropsch reactors at the feed $H_2$:CO ratio below the stoichiometric consumption ratio will result in an even lower exit ratio. This may be desirable to reduce light gas production in the Fischer-Tropsch reactor and increase production of C5+ hydrocarbons. It is preferred to not allow the exit $H_2$:CO ratio to drop below 0.5:1.

The Fischer-Tropsch water 27 produced in the reactor 12 contains a small amount of water soluble organic byproducts such as alcohols and organic acids. These oxygenated chemicals can be concentrated by stripping with steam and/or fuel gas 25 not shown in FIG. 1. The concentrated organic stream can be fed to the process heaters to recover the useful energy or may be used as feed to the syngas generation system or further treated such as with biological treatment or UV light and oxidation with ozone and/or other oxidizing agents known to one skilled in the art, or with adsorbents such as zeolites for removal of trace oxygenates. Such treated water may then be sufficiently clean for discharge or for reuse in the process.

Figure 2:
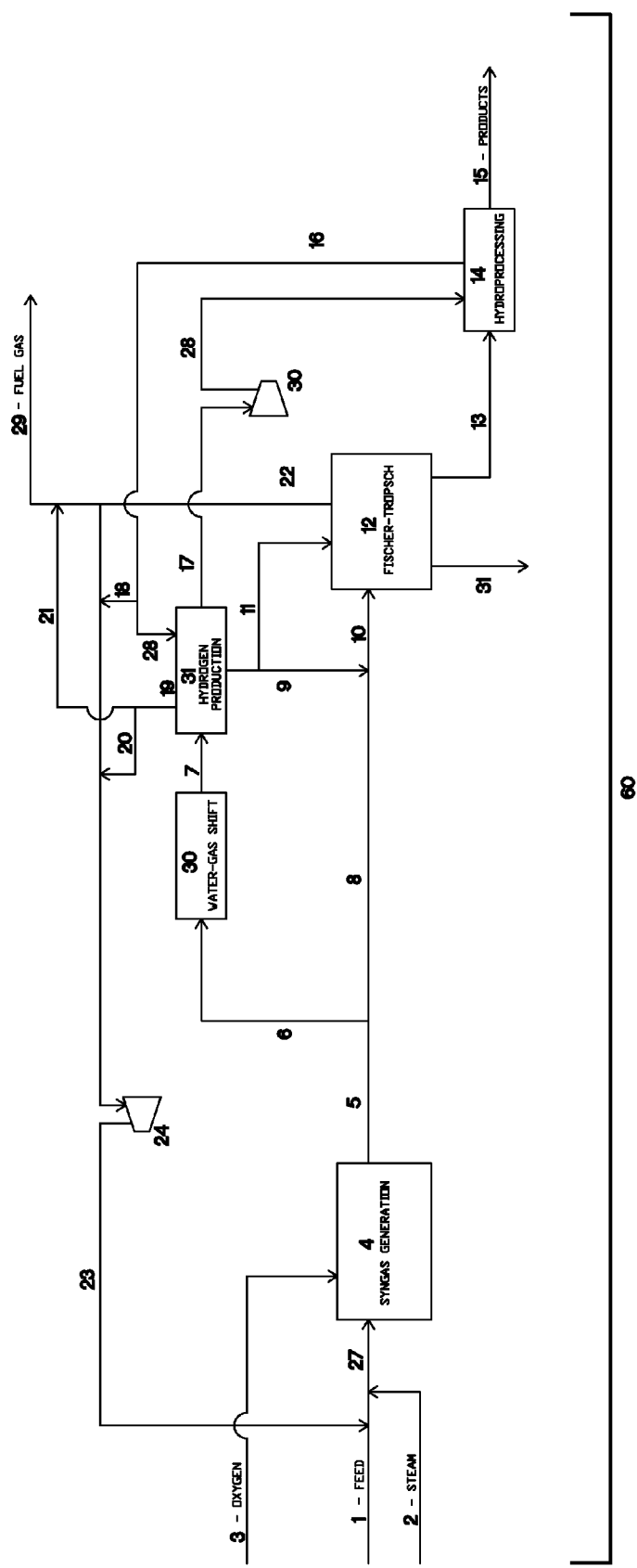
FIG. 2 illustrates a simple process diagram of an alternate embodiment of the present invention.

FIG. 2 illustrates an alternate embodiment of the present invention showing process configuration 60. Carbonaceous material and/or light hydrocarbon gases 1 are combined with a recycle feed. The configuration in FIG. 2 is similar to FIG. 1, except the syngas generator output has a $H_2$:CO ratio below 2:1. In this case, a portion of the syngas shown by line 6 is sent to water gas shift unit 30 to produce the hydrogen needed to balance the process. The water gas shift unit reacts carbon monoxide with water to produce carbon dioxide and hydrogen. As in FIG. 1, a portion of the hydrogen deficient tail gas 22 is used as fuel 29 therefore purging $CO_2$ from the system. Excess hydrogen 18 purged from the hydroprocessing system is added to the remaining tail gas and the combined stream 23 is recycled to the syngas generation unit 4.

Accordingly, the present invention provides an enhanced gas to liquids process which integrates the various process steps for improved efficiency.

What is claimed is:

1. A process to convert carbonaceous materials and/or light hydrocarbon gases or combinations thereof into heavy hydrocarbon products, which process comprises:
   a) converting carbonaceous materials and/or light hydrocarbon gases to synthesis gas with a $H_2$:CO ratio greater than 2.0;
   b) separating a part of the hydrogen from the synthesis gas of step (a);
   c) passing all or a portion of the synthesis gas after hydrogen separation over a cobalt based Fischer-Tropsch catalyst in a Fischer-Tropsch reactor operating at or below the stoichiometric $H_2$:CO ratio, resulting in the production of heavy hydrocarbon products, water and a tail gas comprising mainly light hydrocarbon gases, unreacted syngas, and $CO_2$;
   d) using a portion of the $H_2$ of step (b) for hydroprocessing the Fischer-Tropsch hydrocarbon products;
   e) using a portion of the Fischer-Tropsch tail gas as fuel, thus purging $CO_2$ from the tail gas; and
   f) mixing all or a part of any remaining $H_2$ from step (b) not used for hydroprocessing with all or a part of any remaining Fischer-Tropsch tail gas not used as fuel and recycling this mixed gas stream to step (a).

2. The process of claim 1 wherein if the Fischer-Tropsch section has two or more stages, an additional amount of hydrogen may be added between Fischer-Tropsch stages to provide additional $H_2$:CO ratio control while maintaining the target $H_2$:CO ratio in the tail gas.

3. The process of claim 1 step (a) wherein the syngas is generated is with any type of reforming or gasification reactor such as a coal or biomass gasifier, an autothermal reformer with or without a prereformer or a combination of partial oxidation and steam methane reforming or combinations thereof.

4. The process of claim 1 step (b) wherein the step of separating a part of the hydrogen includes purifying the hydrogen.

5. The process of claim 1 wherein the hydrogen separation of step (b) is done with one or more stages of a hydrogen permeable membrane or with pressure swing adsorption or combinations thereof.

6. The process of claim 1 wherein the water produced in step (c) can be stripped with all or a portion of the fuel gas in step (e) and/or steam to remove soluble organic components which are utilized as fuel for process heaters.

7. The process of claim 6 wherein the stripped water can be further treated for use with conventional water treating processes or combinations thereof.

8. The process of claim 7 wherein conventional treating processes include biological treatment, UV light and ozone, or treatment with oxidation chemicals such as peroxide or trace organic removal over adsorbents such as activated carbon or zeolites or combinations thereof.

9. The process of claim 1 wherein, if the Fischer-Tropsch section has two or more stages, the tail gas from the last stage may be directly recycled to the inlet of the first stage or subsequent stages.

10. A process to convert carbonaceous materials and/or light hydrocarbon gases or combinations thereof into heavy hydrocarbon products which process comprises:
   a) converting carbonaceous materials and/or light hydrocarbon gases to synthesis gas with a $H_2$:CO ratio less than 2.0;
   b) shifting a portion of the synthesis gas of step (a) over a water gas shift ("WGS") catalyst and optionally purifying all or a portion of the hydrogen produced by WGS;
   c) passing all or a portion of the synthesis gas not subjected to WGS over a cobalt based Fischer-Tropsch catalyst in a Fischer-Tropsch reactor operating at or below the stoichiometric $H_2$:CO ratio, resulting in the production of heavy hydrocarbon products, water and a tail gas comprising mainly light hydrocarbon gases, unreacted syngas, and $CO_2$;
   d) if needed, using a portion of the $H_2$ of step (b) to reach the targeted $H_2$:CO ratio at the inlet of the Fischer-Tropsch reactor;
   e) using another portion of the $H_2$ of step (b) for hydroprocessing the Fischer-Tropsch hydrocarbon products;
   f) using a portion of the Fischer-Tropsch tail gas as fuel, thus purging $CO_2$ from the tail gas; and
   g) mixing all or a part of any remaining $H_2$ from step (b) not used for ratio adjustment in step (d) or hydroprocessing in step (e) with all or a part of any remaining Fischer-Tropsch tail gas not used as fuel and recycling this mixed gas stream to step (a).

11. The process of claim 10 wherein at least a portion of water fed to the water gas shift reactor is Fischer-Tropsch water from step (c) that has been concentrated to contain most of the water soluble organic components such as alcohols and acids produced by the Fischer-Tropsch reaction.

12. The process of claim 10 step (b) wherein the hydrogen separation is done with one or more stages of a hydrogen permeable membrane or with pressure swing adsorption or combinations thereof.

13. The process of claim 10 wherein the water produced in step (c) can be stripped with all or a portion of the fuel gas in step (e) and/or steam to remove soluble organic components which are utilized as fuel for process heaters.

14. The process of claim 13 wherein the stripped water can be further treated for use with conventional water treating processes or combinations thereof.

15. The process of claim 14 wherein conventional treating processes include biological treatment, UV light and ozone, or treatment with oxidation chemicals such as peroxide or trace organic removal over adsorbents such as activated carbon or zeolites or combinations thereof.

16. The process of claim 10 wherein, if the Fischer-Tropsch section has two or more stages, the tail gas from the last stage may be directly recycled to the inlet of the first stage or subsequent stages.

* * * * *